(12) United States Patent
Nakajima et al.

(10) Patent No.: US 9,035,127 B2
(45) Date of Patent: May 19, 2015

(54) ABSORBENT ARTICLE

(75) Inventors: Kaiyo Nakajima, Kagawa (JP); Haruki Toda, Kagawa (JP)

(73) Assignee: Unicharm Corporation, Ehime (JP)

( * ) Notice: Subject to any disclaimer, the term of this patent is extended or adjusted under 35 U.S.C. 154(b) by 107 days.

(21) Appl. No.: 13/824,500

(22) PCT Filed: Nov. 14, 2011

(86) PCT No.: PCT/JP2011/076614
§ 371 (c)(1),
(2), (4) Date: Mar. 18, 2013

(87) PCT Pub. No.: WO2012/067217
PCT Pub. Date: May 24, 2012

(65) Prior Publication Data
US 2013/0289510 A1    Oct. 31, 2013

(30) Foreign Application Priority Data

Nov. 19, 2010   (JP) .................................. 2010-259450

(51) Int. Cl.
*A61F 13/15*   (2006.01)
*A61F 13/537*   (2006.01)
(Continued)

(52) U.S. Cl.
CPC ................ *A61F 13/53747* (2013.01); *A61F 2013/530525* (2013.01); *A61F 2013/530562* (2013.01); *A61F 2013/53795* (2013.01); *A61F 13/49426* (2013.01); *A61F 13/535* (2013.01)

(58) Field of Classification Search
CPC . A61F 13/491; A61F 13/4915; A61F 13/537; A61F 13/5376; A61F 13/53704; A61F 2013/4958; A61F 2013/53795; A61F 2013/530525; A61F 2013/530562

USPC .................. 604/368, 372, 382, 385.101
See application file for complete search history.

(56) References Cited

U.S. PATENT DOCUMENTS 4,055,180 A * 10/1977 Karami ........................ 604/368
5,417,680 A *  5/1995 Kimura et al. ........... 604/385.28
(Continued)

FOREIGN PATENT DOCUMENTS

JP    H01-282301 A    11/1989
JP    H09-504206     4/1997
(Continued)

OTHER PUBLICATIONS

International Search Report from corresponding PCT application No. PCT/JP2011/076614 dated Feb. 14, 2012 (2 pgs).

*Primary Examiner* — Lynne Anderson
(74) *Attorney, Agent, or Firm* — Brinks Gilson & Lione (57) ABSTRACT

An absorbent article ensuring that even when excreted urine diffuses by running down the wearer's skin, the urine is prevented from leaking out of the absorbent article. The absorbent article comprises an absorbent sheet that has at least one absorbent polymer-existing region in which the absorbent polymer is sandwiched by at least one liquid-pervious sheet and at least one absorbent polymer-nonexisting region which is free of absorbent polymer. The at least a part of the absorbent sheet is disposed in a rear waist region, and a planar shape of the absorbent polymer-existing region disposed on the rear waist region side of the longitudinal center of the crotch region of the absorbent sheet is a nearly V-shaped with an apex facing in the direction from the front waist region to the rear waist region in the longitudinal direction of the absorbent article.

20 Claims, 10 Drawing Sheets (51) Int. Cl.
  *A61F 13/494* (2006.01)
  *A61F 13/535* (2006.01)
  *A61F 13/53* (2006.01)

(56) References Cited

U.S. PATENT DOCUMENTS

| | | | |
|---|---|---|---|
| 6,372,952 B1* | 4/2002 | Lash et al. | 604/369 |
| 7,663,016 B2* | 2/2010 | Suzuki | 604/378 |
| 7,795,492 B2* | 9/2010 | Vartiainen | 604/378 |
| 2002/0013567 A1* | 1/2002 | Mishima et al. | 604/385.101 |
| 2002/0087136 A1* | 7/2002 | Widlund | 604/379 |
| 2006/0184146 A1 | 8/2006 | Suzuki | |
| 2007/0093164 A1 | 4/2007 | Nakaoka | |

FOREIGN PATENT DOCUMENTS

| | | |
|---|---|---|
| JP | 2002-209940 A | 7/2002 |
| JP | 2003-93441 A | 4/2003 |
| JP | 2004-275225 A | 10/2004 |
| JP | 2004-298330 A | 10/2004 |
| JP | 2004-329644 A | 11/2004 |
| JP | 2004-329664 A | 11/2004 |
| JP | 2005-6954 | 1/2005 |
| JP | 2008-284190 A | 11/2008 |
| JP | 2009-028186 A | 2/2009 |
| JP | 2009-131510 A | 6/2009 |
| JP | 2010-148786 A | 7/2010 |
| WO | WO 95/11651 | 5/1995 |

* cited by examiner

ABSORBENT ARTICLE

RELATED APPLICATION

This application is a 35 U.S.C. §371 national phase filing of International Patent Application No. PCT/JP2011/076614, filed Nov. 14, 2011, through which and to which priority is claimed under 35 U.S.C. §119 to Japanese Patent Application No. 2010-259450, filed Nov. 19, 2010.

TECHNICAL FIELD

The present invention relates to an absorbent article. More specifically, the present invention relates to an absorbent article such as urine-absorbing pad, disposable diaper, toilet training pant and incontinence brief.

BACKGROUND ART

An absorbent article containing an absorption body in a plurality of pockets disposed in the planar direction is known as a conventional technique (see, for example, Patent Literatures 1, 2 and 3). In the absorbent article described in Patent Literature 1, the pocket is formed as a rectangular in the planar view, and an absorbent polymer is movably arranged in the long axis direction of the pocket. In the absorbent article described in Literature 2, pockets having disposed therein a superabsorbent material are discontinuously arranged in a zigzag manner. In the absorbent article described in Literature 3, a plurality of pockets extend in the longitudinal direction and are disposed to align in the width direction, and the width of the pockets is gradually increases toward the longitudinal ends from the longitudinal center.

CITATION LIST

Patent Literature

[Patent Literature 1] Kokai (Japanese Unexamined Patent Publication) No. 2009-131510
[Patent Literature 2] Kohyo (National Publication of Translated Version) No. 9-504206
[Patent Literature 3] Kokai No. 2004-298330

SUMMARY OF THE INVENTION

Technical Problem

However, the conventional absorbent articles described in Patent Literatures 1, 2 and 3 sometimes face a problem that the pocket containing an absorption body is not fitted into the cleft in the boundary portion between right and left buttocks of the wearer and the urine diffused by running down the wearer's skin leaks out of the absorbent article.

Solution to Problem

In order to solve the problem above, the present invention employs the following configuration.

That is, the present invention is an absorbent article consisting of a front waist region, a rear waist region and a crotch region located between the front and rear regions in a longitudinal direction from a front side to a rear side, comprising a liquid-pervious topsheet, a backsheet, an absorption body intervening between the topsheet and the backsheet, and an absorbent sheet between the topsheet and the absorption body, comprising at least one liquid-pervious sheet having sandwiched thereby an absorbent polymer, wherein the absorbent sheet has at least one absorbent polymer-existing region in which an absorbent polymer is sandwiched by at least one liquid-pervious sheet and at least one absorbent polymer-nonexisting region which is free of absorbent polymer, at least a part of the absorbent sheet is disposed in the rear waist region, and a planar shape of the absorbent polymer-existing region disposed on the rear waist region side of the longitudinal center of the crotch region of the absorbent sheet is a nearly V-shaped with an apex facing in the direction from the front waist region to the rear waist region in the longitudinal direction of the absorbent article.

Advantageous Effects of the Invention

According to the present invention, even when the excreted urine diffuses by running down the wearer's skin, the urine is prevented from leaking out of the absorbent article.

DESCRIPTION OF EMBODIMENTS

The absorbent article according to one embodiment of the present invention is described below by referring to the drawings. The absorbent article according to one embodiment of the present invention is a urine-absorbing pad.

Figure 1:
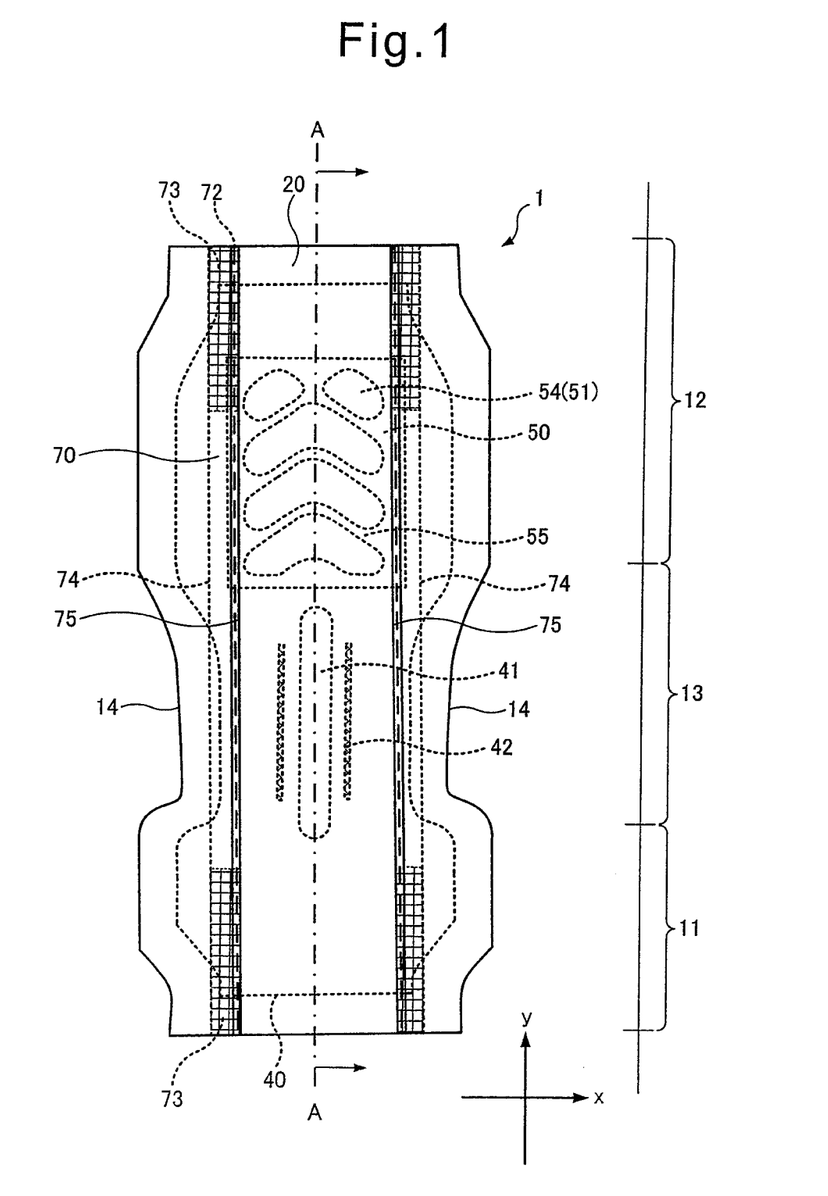
FIG. 1 is a plan view of the absorbent article according to one embodiment of the present invention when viewed from the wearer's skin side.
Figure 2:
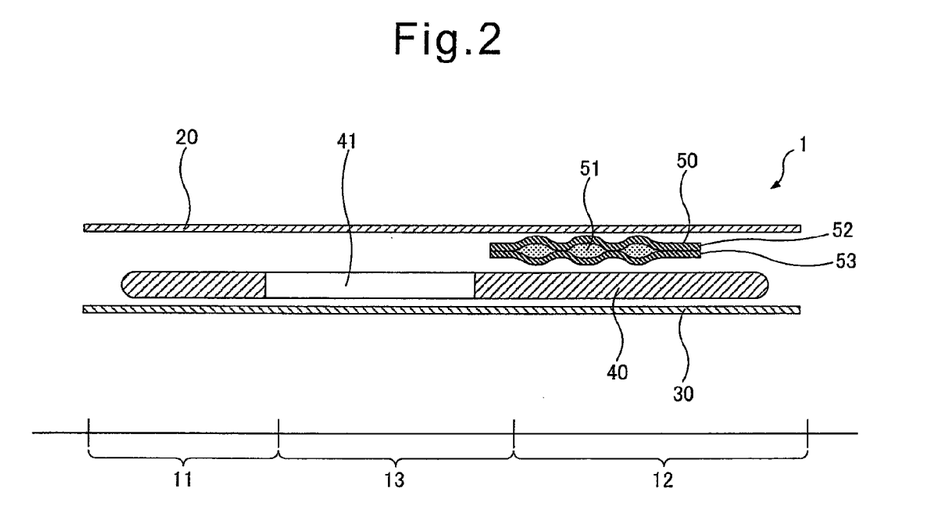
FIG. 2 is a schematic view of the A-A cross-section of FIG. 1.
Figure 3:
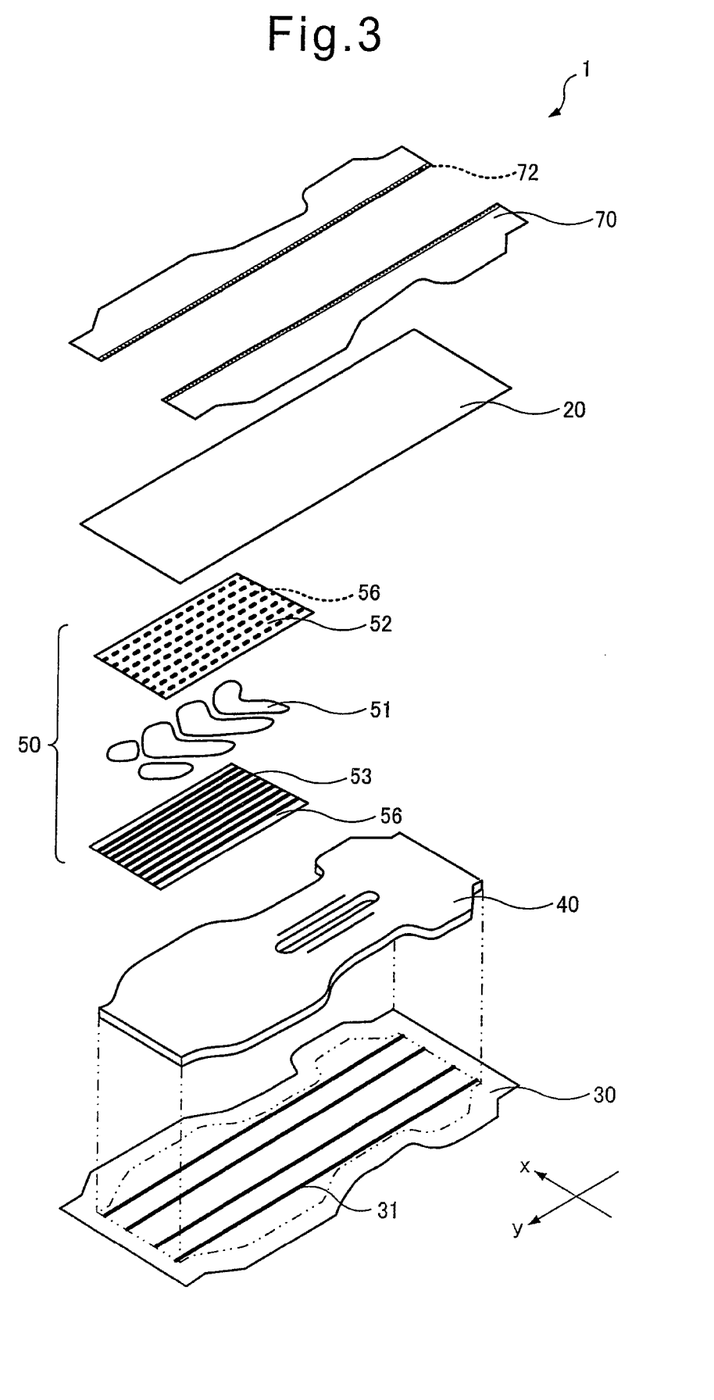
FIG. 3 is an exploded view of the absorbent article according to one embodiment of the present invention.
Figure 4:
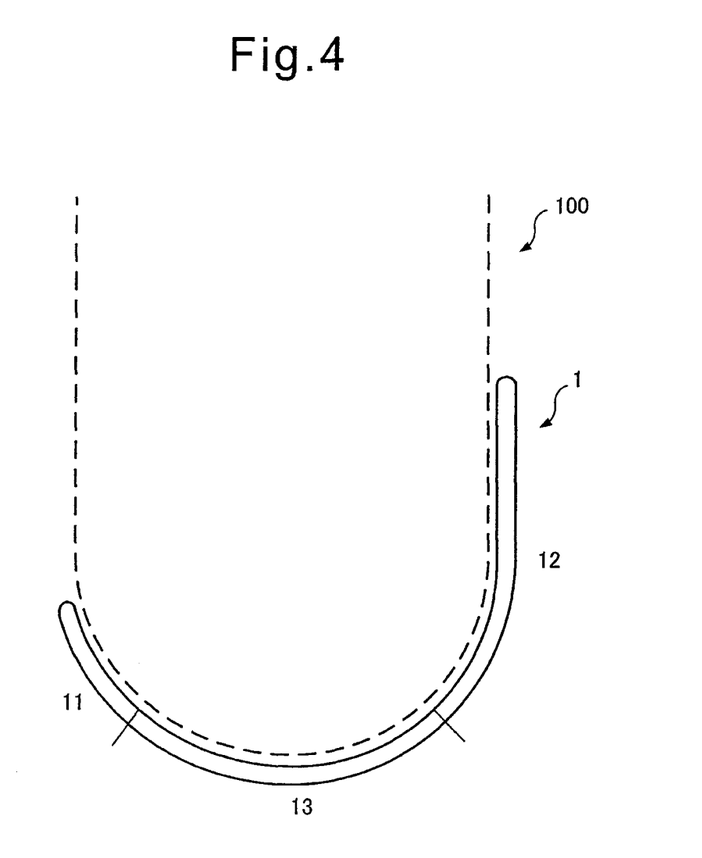
FIG. 4 is a view showing the worn state of the absorbent article according to one embodiment of the present invention.

FIG. 1 is a plan view of the absorbent article according to one embodiment of the present invention when viewed from the wearer's skin side, FIG. 2 is a schematic view of the A-A cross-section of FIG. 1, FIG. 3 is an exploded view of the absorbent article according to one embodiment of the present invention, and FIG. 4 is a view showing the worn state of the absorbent article according to one embodiment of the present invention. The x-axis direction shown in the Figures is the width direction of the absorbent article 1, the y-axis direction is the longitudinal direction of the absorbent article 1, and the xy direction is the planar direction of the absorbent article 1.

As shown in FIG. 1, the absorbent article 1 is divided into a front waist region 11, a rear waist region 12, and a crotch region 13 between the front waist region 11 and the rear waist region 12. Here, the front waist region 11 side of the absorbent article 1 is taken as the front side of the absorbent article 1 and the rear waist region 12 side of the absorbent article 1 is taken as the rear side of the absorbent article 1. As shown in FIG. 4, the crotch region 13 is a region applied to the crotch of a wearer 100 when the absorbent article is worn, the front waist region 11 is a region on the front belly side relative to the crotch region 13, and the rear waist region 12 is a region on the rear side relative to the crotch region 13. In the crotch region 13, the side part 14 (see FIG. 1) is bent or curved to decrease the length in the width direction of the absorbent article 1. The "crotch part" as used herein indicates the region between both femoral areas of the wearer when the wearer stands erect. Accordingly, the front waist region 11 covers the belly side of the wearer, and the rear waist region 12 covers the buttocks of the wearer. That is, the crotch region 13 is a region applied to the wearer's crotch, the front waist region 11 is a region covering the front side relative to the wearer's crotch, and the rear waist region 12 is a region covering the rear side relative to the wearer's crotch part.

The absorbent article 1 in one embodiment of the present invention comprises a liquid-pervious topsheet 20, a backsheet 30 provided at the position opposing the topsheet 20, and an absorption body 40 provided between the topsheet 20 and the backsheet 30. An absorbent sheet 50 is disposed between the topsheet 20 and the absorption body 40, and on both widthwise sides of the topsheet 20, a leak-preventive cuff 70 is disposed.

The topsheet 20 is a liquid-pervious sheet allowing the excreted urine to permeate therethrough and is provided on the surface coming into contact with the wearer's skin so as to feel smooth and soft on the skin when the wearer wears the absorbent article 1. Accordingly, the topsheet 20 preferably has a function of giving a soft and comfortable touch to skin. For example, the topsheet 20 may be produced using a fine fiber and have smooth surface and large latitude for deformation. Generally, a nonwoven fabric is used for the topsheet 20. Examples of the nonwoven fabric used for the topsheet 20 include a spunbond nonwoven fabric, a point bond nonwoven fabric and an air-through nonwoven fabric. The topsheet 20 is disposed across the front waist region 11, the crotch region 13 and the rear waist region 12. The shape of topsheet 20 may be a rectangle.

The backsheet 30 is a liquid-impervious sheet allowing no permeation of urine and is provided to prevent the excreted urine from leaking outside. The material of the backsheet 30 is not particularly limited as long as it is a material allowing no permeation of excreted urine. For example, a waterproof-treated nonwoven fabric, a plastic film composed of polyethylene or the like, or a composite material of nonwoven fabric and plastic film can be used for the backsheet 30. Also, in order to prevent the absorbent article 1 in wearing from causing stuffiness due to exhalation of water vapor through the backsheet 30, a breathable film may be used for the backsheet 30. Incidentally, in the case of a urine-absorbing pad or the like used inside a diaper, the backsheet 30 need not be liquid-impervious. The backsheet 30 is disposed across the front waist region 11, the crotch region 13 and the rear waist region 12.

The absorption body 40 has a function of absorbing and holding the excreted urine. The absorption body 40 includes, for example, an absorption body composed of a fluffed pulp or an air-laid nonwoven fabric and a super-absorbent polymer (SAP). The absorption body 40 can alternatively include, for example, a chemical pulp, a cellulose fiber, an artificial cellulose fiber such as rayon and acetate, or a fiber network absorption body using a synthetic fiber (including a composite fiber) such as polyolefin, polyester and polyamide, or a foam absorption body using a foam material such as polyurethane, instead of using a fluffed pulp.

The absorption body 40 has a nearly similar shape as the backsheet 30 with the size of the absorption body 40 being small compared with the backsheet 30. The absorption body 40 is disposed across the front waist region 11, the crotch region 13 and the rear waist region 12. The absorption body 40 has a penetration part 41 and compressed grooves 42. The penetration part 41 may be a hole penetrating the absorption body 40 in the thickness direction and at the widthwise central position of the absorption body 40, the penetration part 41 longitudinally extends across the crotch region 13 up to or into the front waist region 11. However, the penetration part 41 is kept from longitudinally extending to the region of the absorption body 40, where the absorbent sheet 50 is disposed. The compressed grooves 42 are disposed on both sides of the penetration part 41 and are aligned with each other and longitudinally extend across the crotch region 13 and are indented from the topsheet side surface of the absorption body 40. The longitudinal length of the compressed grooves 42 are short compared with the longitudinal length of the penetration part 41. The compressed groove 42 is formed by heating•pressurizing the absorption body 40 toward the backsheet 30 side surface from the topsheet 20 side surface of the absorption body 40. The absorption body 40 is adhered to the backsheet 30 by a hot-melt adhesive (HMA) 31. The absorption body may be in the shape of a rectangular, oval or other shape instead of having a nearly similar shape to the backsheet 30.

The absorbent sheet 50 is an absorbent sheet where an absorbent polymer 51 is sandwiched between two liquid-pervious sheets 52 and 53. Incidentally, the absorbent sheet may be produced by sandwiching an absorbent polymer by three or more liquid-pervious sheets. For example, the absorbent polymer is placed between each of the sheets or between the sheets near the body or between the sheets remote from the body or between all of them. The absorbent sheet 50 is joined with the topsheet 20 and the absorption body 40. Also, the absorbent sheet may be produced by sandwiching an absorbent polymer by a folded liquid-pervious sheet. That is to say, the absorbent sheet is produced by sandwiching an absorbent polymer by at least one liquid-pervious sheet. The absorbent polymer is an absorbent polymer capable of absorbing water and is, for example, an absorbent macromolecular polymer having a three-dimensional network structure formed by appropriate crosslinking of water-soluble macromolecules. Such an absorbent macromolecular polymer absorbs several hundreds or thousands of times as much water as the volume before absorbing water but is substantially water-insoluble and does not release the once absorbed water even when some pressure is applied. Examples of the absorbent polymer include starch-based, acrylic acid-based or amino acid-based particulate or fibrous polymers. The absorbent polymer is the absorbent polymer which is in general use for a diaper. An absorbent polymer 51 is sandwiched by two liquid-pervious sheets 52 and 53 and then, these two liquid-pervious sheets 52 and 53 are joined, whereby the absorbent sheet 50 is produced. Accordingly, in order to prevent the absorbent polymer from spilling after sandwiching the absorbent polymer 51 between two liquid-pervious sheets 52 and 53, the particle diameter of the absorbent polymer is preferably not smaller than the fiber interstices of the liquid-pervious sheets 52 and 53. For example, the amount of the absorbent polymer 51 between two liquid-pervious sheets 52 and 53 is 0.0125 to 0.0250 $g/cm^2$. The absorbent polymer 51 is the absorbent polymer generally used for the absorbent article. For example the absorbent polymer 51 of 0.5 g can absorb water of 60 g and hold water of 40 g. The gel strength of the absorbent polymer 51 is preferably high so that the absorbent polymer 51 is not smashed.

For example, a spunbond nonwoven fabric, a point bond nonwoven fabric, an air-through nonwoven fabric or an SMS (spunbond-melt blown-spunbond) nonwoven fabric may be used for the liquid-pervious sheets 52 and 53. Out of two liquid-pervious sheets 52 and 53, the liquid-pervious sheet 52 disposed on the topsheet 20 side is referred to as an upper liquid-pervious sheet, and the liquid-pervious sheet 53 disposed on the absorption body 40 side is referred to as a lower liquid-pervious sheet. Out of two liquid-pervious sheets 52 and 53, at least the upper liquid-pervious sheet 52 has hydrophilicity. The lower liquid-pervious sheet 53 may also have hydrophilicity. When the air-through nonwoven fabric is used as the liquid-pervious sheets 52 and 53, the basis weight of the liquid-pervious sheets 52 and 53 is preferably 25 to 30 $g/m^2$. Due to the basis weight of the liquid-pervious sheets 52 and 53, an adhesive strength between the liquid-pervious sheets 52 and 53 can increase, and the liquid-pervious sheets 52 and 53 are not separated from each other due to swelling of the absorbent polymer 51 provided between them. Among the spunbond nonwoven fabric, the air-through nonwoven fabric and the SMS nonwoven fabric, the air-through nonwoven fabric is most preferably used as the liquid-pervious sheets 52 and 53, since the air-through nonwoven has an unevenness surface and the particle of SAP can be fit into a hollow in the surface. The air-through nonwoven fabric preferably comprises at least two types of fibers the melting points of which are different from each other. For example, the air-through nonwoven fabric preferably comprises polyethylene fibers and polypropylene fibers. Due to the at least two types of fibers, the liquid-pervious sheets 52 and 53 are not torn-off when embossing the liquid-pervious sheets 52 and 53, since one of the two types of fibers do not melt when embossing the liquid-pervious sheets 52 and 53. The liquid-pervious sheets 52 and 53 are preferably stuck together with a hot melt adhesive.

On the absorbent polymer 51-sandwiching surfaces of the upper liquid-pervious sheet 52 and the lower liquid-pervious sheet 53, a plurality of longitudinally extending adhesive parts 56 aligned in the width direction are provided. For example, the adhesive of the adhesive parts includes styrene-ethylene-butadiene-styrene copolymer, styrene-butadiene-styrene copolymer and styrene-isoprene-styrene copolymer. Incidentally, the adhesive part 56 may be provided on the absorbent polymer 51-sandwiching surface of at least one liquid-pervious sheet out of the upper liquid-pervious sheet 52 and the lower liquid-pervious sheet 53. Also, the adhesive part 56 may be provided only in the region of the upper liquid-pervious sheet 52 and/or the lower liquid-pervious sheet 53, which corresponds to the later-described absorbent polymer-existing region 54 (see FIGS. 1, 5, 6, and 10). That is, the adhesive part 56 is provided on the liquid-pervious sheet 52 and 53 at least in the absorbent polymer-existing region 54 of the absorbent sheet 50. The adhesive part 56 is formed, for example, by coating a hot-melt adhesive in a streak manner. Thanks to this adhesive, the absorbent polymer 51 is fixed to the upper liquid-pervious sheet 52 and the lower liquid-pervious sheet 53. In turn, the absorbent polymer 51 is evenly fixed in the later-described absorbent polymer-existing region 54. The coating method is not limited to the streaky pattern coating method as long as it is a coating method capable of providing a region absent of the adhesive part 56, for example, intermittently disposing the adhesive part, since permeability of urine in the adhesive part 56 is poor. A non-contact coating method such as omega pattern coating may be also employed. The adhesive part-to-adhesive part distance between adjacent adhesive parts of the adhesive parts 56 provided on the lower liquid-pervious sheet 53 is small compared with the adhesive part-to-adhesive part distance of the adhesive parts 56 provided on the upper liquid-pervious sheet 52. Thanks to this configuration, permeation of the urine coming from the topsheet side is facilitated, and the urine coming from the absorption body side is hardly allowed to return. For example, the width of the adhesive part 56 in the upper liquid-pervious sheet 52 is 5 mm and the pitch of the adhesive part 56 is 15 mm, and the width of the adhesive part 56 in the lower liquid-pervious sheet 53 is 1 mm and the pitch of the adhesive part 56 is 2 mm. Since the surface area of the adhesive part 56 of the upper liquid-pervious sheet 52 is small, the liquid can easily pass through the upper liquid-pervious sheet 52. For example, the adhesive of the adhesive part 56 is a hot melt adhesive generally used for an absorbent article. The adhesive part 56 prevents the absorbent polymer from moving before embossing the liquid-pervious sheets and from going too far to on side when carrying the absorbent article.

When streaky adhesive parts 56 are colored blue or another color are provided on the upper liquid-pervious sheet 52 and the lower liquid-pervious sheet 53, a striped pattern with blue or another color is imparted to the absorbent article 1 and in turn, the appearance of the absorbent article 1 is improved. Incidentally, the adhesive part 56 may be provided only on the absorbent polymer 51-sandwiching surface of the lower liquid-pervious sheet 53. By providing the adhesive part 56 on the upper liquid-pervious sheet 52 and/or the lower liquid-pervious sheet 53, the absorbent polymer 51 can be kept from moving in the absorbent sheet 50 before the absorbent polymer 51 swells.

In the absorbent sheet 50, the absorbent polymer 51 is disposed in parts in a plurality of regions 54 (herein, referred to as an "absorbent polymer-existing region"), and a region 55 having not disposed therein the absorbent polymer 51 (hereinafter, referred to as an "absorbent polymer-nonexisting region") is provided between respective absorbent polymer-existing regions 54. Thanks to this configuration, even when the absorbent polymer 51 in the absorbent polymer-existing region 54 fully swells by absorbing urine and cannot absorb urine any more, the urine passes through the absorbent polymer-nonexisting region 55 and is absorbed by the absorption body 40.

As described above, the region where the absorbent polymer 51 is sandwiched between the upper liquid-pervious sheet 52 and the lower liquid-pervious sheet 53 is the absorbent polymer-existing region 54, and the region where the upper liquid-pervious sheet 52 and the lower liquid-pervious sheet 53 are joined without sandwiching the absorbent polymer 51 between the upper liquid-pervious sheet 52 and the lower liquid-pervious sheet 53 is the absorbent polymer-nonexisting region 55. Joining of these upper liquid-pervious sheet 52 and lower liquid-pervious sheet 53 with each other requires strength high enough to withstand the expansion force due to swelling of the absorbent polymer 51. Otherwise, the upper liquid-pervious sheet 52 and the lower liquid-pervious sheet 53 are sometimes separated from each other due to swelling of the absorbent polymer 51 to produce a gap between the two liquid-pervious sheets 52 and 53 and allow intrusion of the absorbent polymer 51 into the gap, resulting in disappearance of the absorbent polymer-nonexisting region 55. For joining the upper liquid-pervious sheet 52 and the lower liquid-pervious sheet 53 with desired strength, a heat seal, a sonic seal, an adhesive or the like can be used.

In the case of joining by a heat seal, for improving the permeability of urine in the absorbent polymer-nonexisting region 55, the heat sealing may be performed to create heated•pressurized portions having a uniform dot shape by using a pin having a circular or rectangular cross-sectional shape. In the case of joining the upper liquid-pervious sheet 52 and the lower liquid-pervious sheet 53 by using an adhesive, the adhesive is preferably of a type capable of exerting the strength even when wetted, because the upper liquid-pervious sheet 52 and the lower liquid-pervious sheet 53 are in a wet state when the absorbent polymer 51 is swelled. The expansion force due to swelling of the absorbent polymer 51 depends on the amount and the type of the absorbent polymer 51. For example, the expansion force in 35 cm$^2$ of the absorbent polymer of 0.3 g which absorbs the water of 60 g is 1.0 N/25 mm. Pell strength of the upper liquid-pervious sheet 52 and the lower liquid-pervious sheet 53 joined each other can be measured as described below. A sample is prepared by cutting the liquid-pervious sheets 52 and 53 stuck together with a hot melt adhesive into a rectangle shape with a width of 25 mm having a longitudinal direction perpendicular to stuck portion. The sample is soaked into water for 1 minute. Then, the adhesion test of the sample is carried out in the condition of 100 mm/min with a tensile tester.

The planar shape of the absorbent polymer-existing region 54 disposed on the rear waist region 12 side relative to the longitudinal center of the crotch region 13 of the absorbent sheet 50 is a nearly V-shape projecting in the direction from the front waist region 11 to the rear waist region 12 in the longitudinal direction of the absorbent article 1 and extending in the width direction of the absorbent article 1. That is, the planar shape of the absorbent polymer-existing region 54 is a nearly V-shape with the apex facing in the direction from the front waist region 11 to the rear waist region 12 in the longitudinal direction of the absorbent article 1. However, the absorbent polymer-existing region 54 most remote from the front waist region 11 may have a shape formed by cutting out the widthwise center of the nearly V-shape. Three absorbent polymer-existing regions 54 are aligned in the longitudinal direction of the absorbent article 1. More than three absorbent polymer-existing regions may be aligned in the longitudinal direction of the absorbent article 1 and less than three absorbent polymer-existing regions may be aligned in the longitudinal direction of the absorbent article 1. The forefront of the longitudinally projected portion of the absorbent polymer-existing region 54 is located on the straight line passing the widthwise center of the absorbent article and extending in the longitudinal direction.

Figure 5:
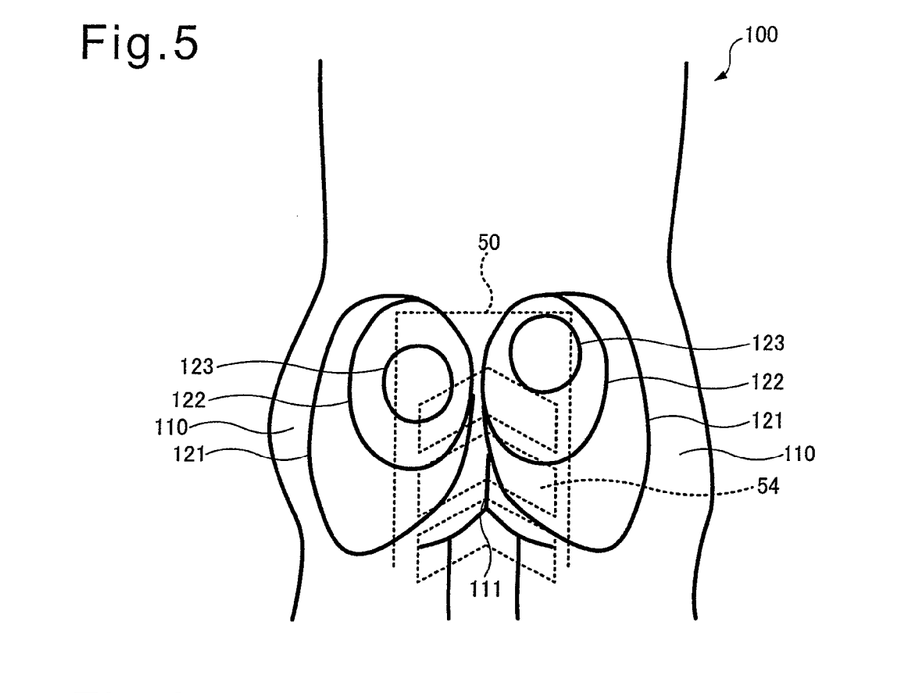
FIG. 5 is a view showing the body pressure distribution of the wearer's buttocks.

FIG. 5 is a view showing the body pressure distribution of the wearer's buttocks. The curved lines 121 to 123 shown on the buttocks 110 of the wearer 100 indicate an isobaric curve of the body pressure. FIG. 5 also shows the position of the absorbent sheet 50 when the absorbent article 1 is worn. The absorbent polymer-existing region 54 of the absorbent sheet 50 has a shape following the isobaric curve of body pressure of the wearer 100. Thanks to this shape, when the absorbent polymer-existing region 54 deforms due to the body pressure of the wearer 100 to further bend the nearly V-shape, the absorbent polymer-existing region 54 comes to fit the recess 111 in the boundary portion of right and left buttocks 110 of the wearer 100 and a gap is scarcely produced between the wearer and the absorbent article 1.

Figure 6:
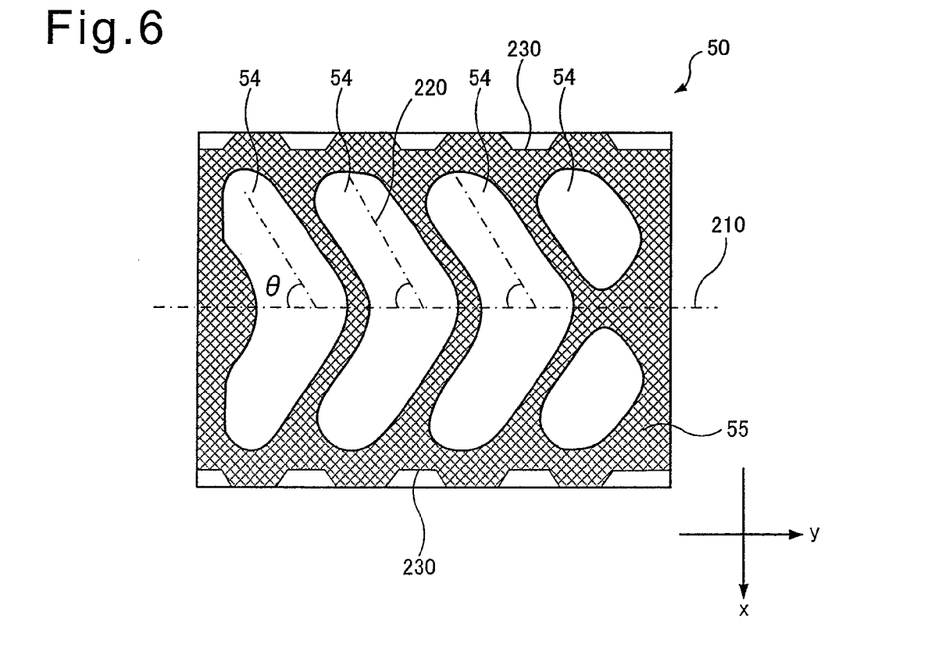
FIG. 6 is a view showing the gradient of the absorbent polymer-existing region with respect to the straight line extending in the longitudinal direction of the absorbent article.

FIG. 6 is a view showing the gradient of the absorbent polymer-existing region with respect to the straight line extending in the longitudinal direction of the absorbent article. In FIG. 6, the chain line 210 indicates the straight line passing the widthwise center of the absorbent article 1 and extending in the longitudinal direction, the chain line 220 indicates the direction in which the absorbent polymer-existing region 54 is tilted, and θ indicates the angle of the gradient of the absorbent polymer-existing region 54 with respect to the straight line 210 extending in the longitudinal direction of the absorbent article 1. The gradient θ of the absorbent polymer-existing region 54 is preferably at an angle between 45° and 80°. If the gradient θ of the absorbent polymer-existing region 54 is less than 45°, the absorbent polymer-nonexisting region 55 is caused to too much extend in the longitudinal direction of the absorbent article 1, as a result, the excrement such as urine is liable to pass through the absorbent polymer-nonexisting region 55 and flow to the longitudinal end on the rear waist side 12 of the absorbent article 1 and the excrement sometimes leaks from the end of the absorbent article 1. If the gradient θ of the absorbent polymer-existing region 54 exceeds 80°, the shape of the absorbent sheet 50 does not follow the wearer's buttocks shape and the body pressure distribution of the buttocks, and a gap may be produced between the wearer's buttocks and the absorbent article 1.

When the absorbent polymer 51 of the absorbent sheet absorbs the excreted urine, the absorbent polymer 51 swells and the absorbent polymer-existing region 54 bulges to the topsheet 20 side. In turn, the absorbent sheet 50 comes to more fit the buttocks 110 of the wearer 100 and a gap is hardly produced between the wearer 100 and the absorbent article 1.

The absorbent sheet 50 is disposed in a part of at least the rear waist region 12. Furthermore, the absorbent sheet 50 is preferably disposed in at least a part of the rear waist region 12. Thanks to this configuration, when the wearer's urination orifice is contacted with the absorbent article 1, the urine excreted without permeating through the absorbent sheet 50 can be directly absorbed by the absorption body 40, and when the wearer's urination orifice is not contacted with the absorbent article 1, the urine can be absorbed by the absorbent sheet 50.

Figure 7:
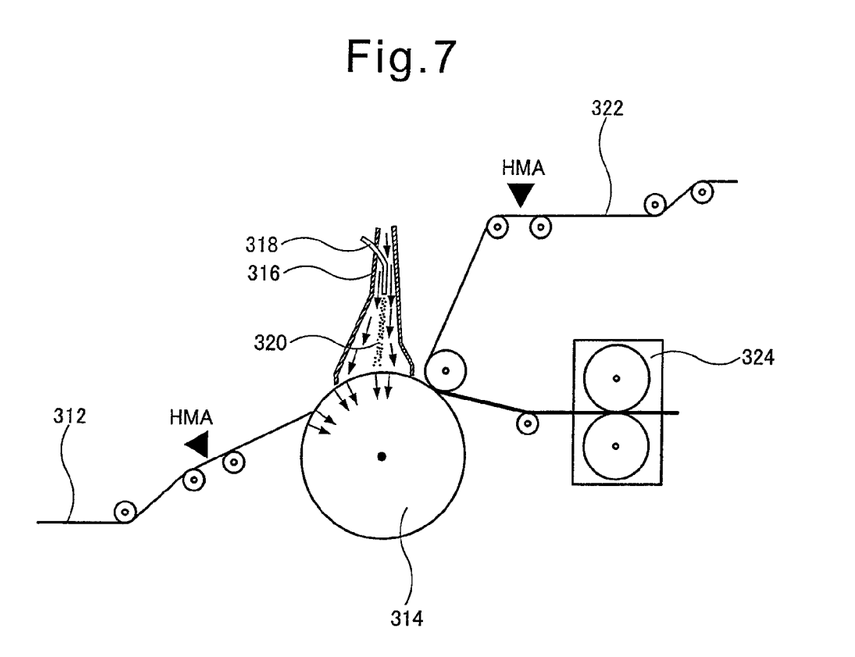
FIG. 7 is a view for explaining the production method of the absorbent sheet.

The production method of the absorbent sheet 50 is described below by referring to FIG. 7. A lower liquid-pervious sheet 312 is coated with a hot-melt adhesive in a streak manner and then delivered to a suction drum 314. The suction drum 314 suctions only the pattern portion of an absorbent polymer-existing region 54. This enables an absorbent polymer 320 fed through a polymer charge tube 318 of a duct 316 to concentrate in the pattern portion of an absorbent polymer-existing region 54, as a result, the absorbent polymer 320 is deposited in the region corresponding to the absorbent polymer-existing region 54 of the lower liquid-pervious sheet 312. An upper liquid-pervious sheet 322 is coated with a hot-melt adhesive in a streak manner and then delivered to a suction drum 314. The upper liquid-pervious sheet 322 is then stacked on the lower liquid-pervious sheet 312 having deposited thereon the absorbent polymer 320, and the stack is delivered to a heat sealing device 324. In the heat sealing device 324, out of the liquid-pervious sheets 312, 322 sandwiching the absorbent polymer 320, the region corresponding to the absorbent polymer-nonexisting region is heat-sealed. The heat-sealed liquid-pervious sheet is cut into the shape of an absorbent sheet by a cutter not shown, whereby an absorbent sheet is completed.

In the above-described production method of an absorbent sheet 50, a hot-melt adhesive is coated on the upper liquid-pervious sheet 322 and the lower liquid-pervious sheet 312, and this is performed for preventing the deposited absorbent polymer 320 from slipping from its position during the period after the absorbent polymer 320 is deposited on the lower liquid-pervious sheet 312 until the upper liquid-pervious sheet 322 and the lower liquid-pervious sheet 312 sandwiching the absorbent polymer 320 are heat-sealed.

In the case of forming the absorbent polymer-nonexisting region 55 by a heat seal, when the linear pressure in the width direction of the heat seal is constant, uniform seal strength is achieved in whole. For this reason, the linear pressure in the width direction of the heat seal is preferably constant. For keeping a uniform linear pressure in the width direction of the heat seal, the total of the widthwise lengths of regions to be sealed is made constant. For example, as described above, absorbent polymer-existing regions 54 are formed in a nearly V-shape and aligned in the longitudinal direction, whereby the total of the widthwise lengths of the absorbent polymer-nonexisting regions 55 can be made substantially constant. Also, as shown in FIG. 6, the distance between both widthwise edge parts 230 of the absorbent polymer-nonexisting region 55 may be increased or decreased so that the total of the widthwise lengths of the absorbent polymer-nonexisting regions 55 can be made more constant.

Furthermore, in the case of forming the absorbent polymer-nonexisting region 55 by a heat seal, it is preferred that the linear pressure in the widthwise direction of the heat seal does not rapidly change. In order to gradually increase the non-heat-sealed region in the longitudinal direction when the heat-sealing of the absorbent polymer-sandwiching liquid-pervious sheets proceeds longitudinally, the absorbent polymer-existing region 54 most remote from the front waist region 11 is designed to have a shape formed by cutting out the widthwise center of the nearly V-shape.

The leak-preventive cuffs 70 prevent the excreted urine from leaking outside at widthwise positions of the absorbent article 1. In both widthwise side parts of the absorbent article 1, a longitudinally extending leak-preventive cuffs 70 is disposed. A hydrophobic nonwoven fabric such as SMS nonwoven fabric is used for the leak-preventive cuff 70. A leak-preventive material such as waterproof film may be also used in place of SMS nonwoven fabric. The leak-preventive cuffs 70 are joined with the topsheet 20 or the backsheet 30 in the widthwise side parts of the absorbent article 1 by using a hot-melt adhesive and have a base end parts 74 and a free end parts 75. The base end parts 74 are joined with the widthwise side parts of the absorbent article 1 and can be fixed using a heat seal in place of a hot-melt adhesive. The base end parts 74 may be also located at the sides edge or backsheet surface of the absorbent article 1. The free end parts 75 are located on the widthwise inner side of the absorbent article 1 relative to the base end parts 74. An elastic body 72 capable of extending in the longitudinal direction and fixed in an extended state is provided near the edge parts 71 of the free end parts 75 of each of the leak-preventive cuffs 70. Also, the regions 73 on the longitudinal end sides of the free end parts 75 of the leak-preventive cuffs 70 are joined with the topsheet 20 and the backsheet 30 by using a hot-melt adhesive. When the elastic bodies 72 develops their contractive force, the free end part 75 of the leak-preventive cuffs 70 excluding the region 73 on the lengthwise end sides of the leak-preventive cuffs 70 rise from the topsheet 20 due to the contractive force of the elastic bodies 72 and prevent the excreted urine from leaking at widthwise positions of the absorbent article 1. The leak-preventive cuffs 70 need not be disposed over the entire length of the absorbent article 1 and may be sufficient if they are disposed at least across the rear waist region 12.

Absorption of the excreted urine by the absorption article 1 in one embodiment of the present invention is described below by referring to the drawings.

Figure 8:
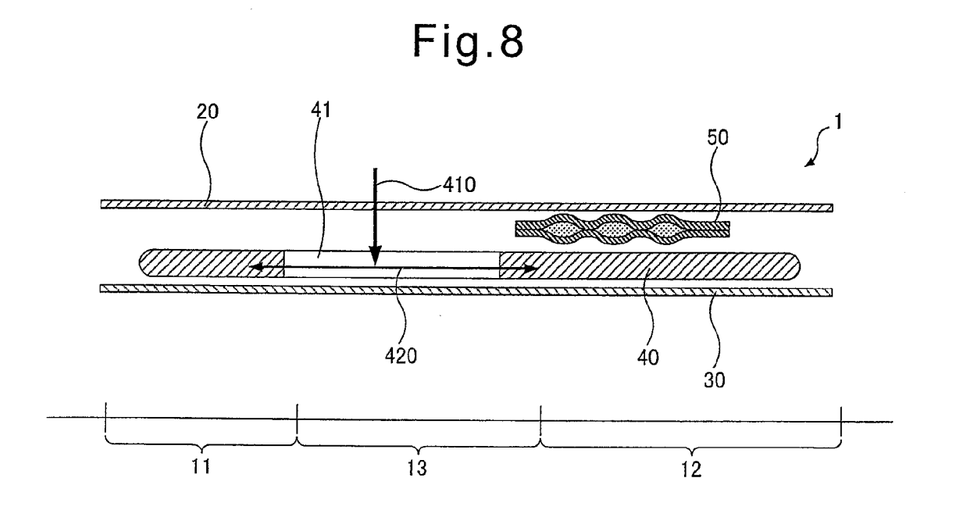
FIG. 8 is a view for explaining absorption of the excreted urine by the absorbent article according to one embodiment of the present invention when the wearer's urination orifice is contacted with the absorbent article.

In the case where the wearer's urination orifice is contacted with the absorbent article 1, as shown in FIG. 8, the excreted urine passes (arrow 410) through the topsheet 20 at a portion of the crotch region 13, where the absorbent sheet 50 is not disposed, and reaches the absorption body 40. The urine reached the absorption body 40 is absorbed from the absorbent sheet 50 side surface of the absorption body 40. Some urine reached (arrow 410) the penetration part 41 of the absorption body 40 is absorbed (arrow 420) from the side wall of the penetration part 41, and some urine reached the compressed groove 42 of the absorption body 40 is absorbed from the side wall of the compressed groove 42. By providing the penetration part 41 and/or the compressed groove 42 in the absorption body 40, the excreted urine is allowed to readily move in the longitudinal direction and therefore, diffusion of the excreted urine to the absorption body 40 is accelerated.

When the wearer lies on his(her) back and a body pressure is imposed on the rear waist region 12 of the absorbent article 1 from the wearer's buttocks, the urine absorbed in the absorption body 40 seeps but the seeped urine hardly reaches the wearer's skin side due to the absorbent sheet 50, because the urine seeped from the absorption body 40 due to a body pressure is absorbed by the absorbent sheet 50. On the other hand, in the region of the crotch region 13, where the absorbent sheet 50 is not disposed, and the front waist region 11, a pressure is less likely to be imposed on the absorbent article 1 and it is lessened that the urine absorbed by the absorption body 40 seeps from the absorption body 40. In turn, the wearer's skin is kept dry and comfortable even after the urine is excreted, and the wearer's skin can be protected against irritation due to the excreted urine.

Figure 9:
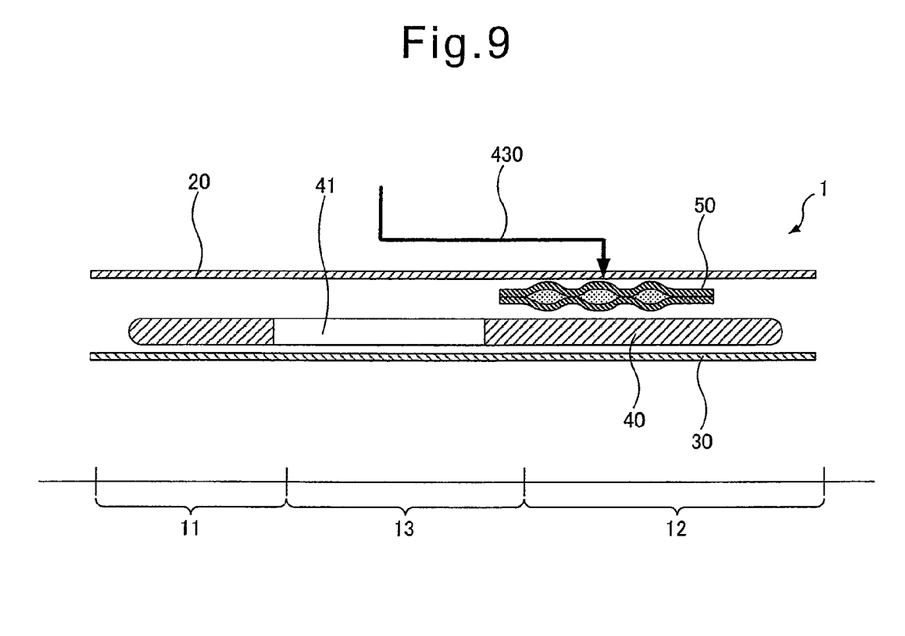
FIG. 9 is a view for explaining absorption of the excreted urine by the absorbent article according to one embodiment of the present invention when the wearer's urination orifice is not contacted with the absorbent article.

In the case where the wearer's urination orifice is not contacted with the absorbent article 1, for example, when a wearer lies on his(her) back, as shown in FIG. 9, the excreted urine runs down the wearer's skin to reach the topsheet 20 in the portion of the crotch region 13 and/or the rear waist region 12, where the absorbent sheet 50 is disposed (arrow 430). The urine reached the topsheet 20 is absorbed by the absorbent sheet 50. Also, as described above, the absorbent polymer has a property of not releasing the once absorbed water even upon application of some pressure and therefore, even when the wearer lies on his(her) back and a body pressure is imposed on the rear waist region 12 of the absorbent article 1 from the wearer's buttocks, the urine absorbed by the absorbent sheet 50 is less likely to seep from the absorbent sheet 50 due to the body pressure. In turn, the wearer's skin is kept dry and comfortable even after the urine is excreted, and the wearer's skin can be protected against irritation from the excreted urine. Furthermore, the excreted urine does not leak out of the absorbent article 1.

As described above, three absorbent polymer-existing regions 54 are aligned in the longitudinal direction of the absorbent article 1. Accordingly, the urine having failed to be absorbed by the absorbent polymer in the first absorbent polymer-existing region 54 shown in FIG. 6 can be absorbed by the absorbent polymers in the second and third absorbent-polymer existing regions 54, so that the urine diffused by running down the wearer's skin can be prevented from leaking outside at the longitudinally end portion of the absorbent article 1. Also, the absorbent polymer-existing region 54 is extending in the width direction and a longitudinally extending groove is not present, so that the urine diffused by running own the wearer's skin can be prevented from leaking outside at a portion in the longitudinal direction of the absorbent article.

The above-described absorbent article 1 in one embodiment can be modified as follows.

Figure 10:
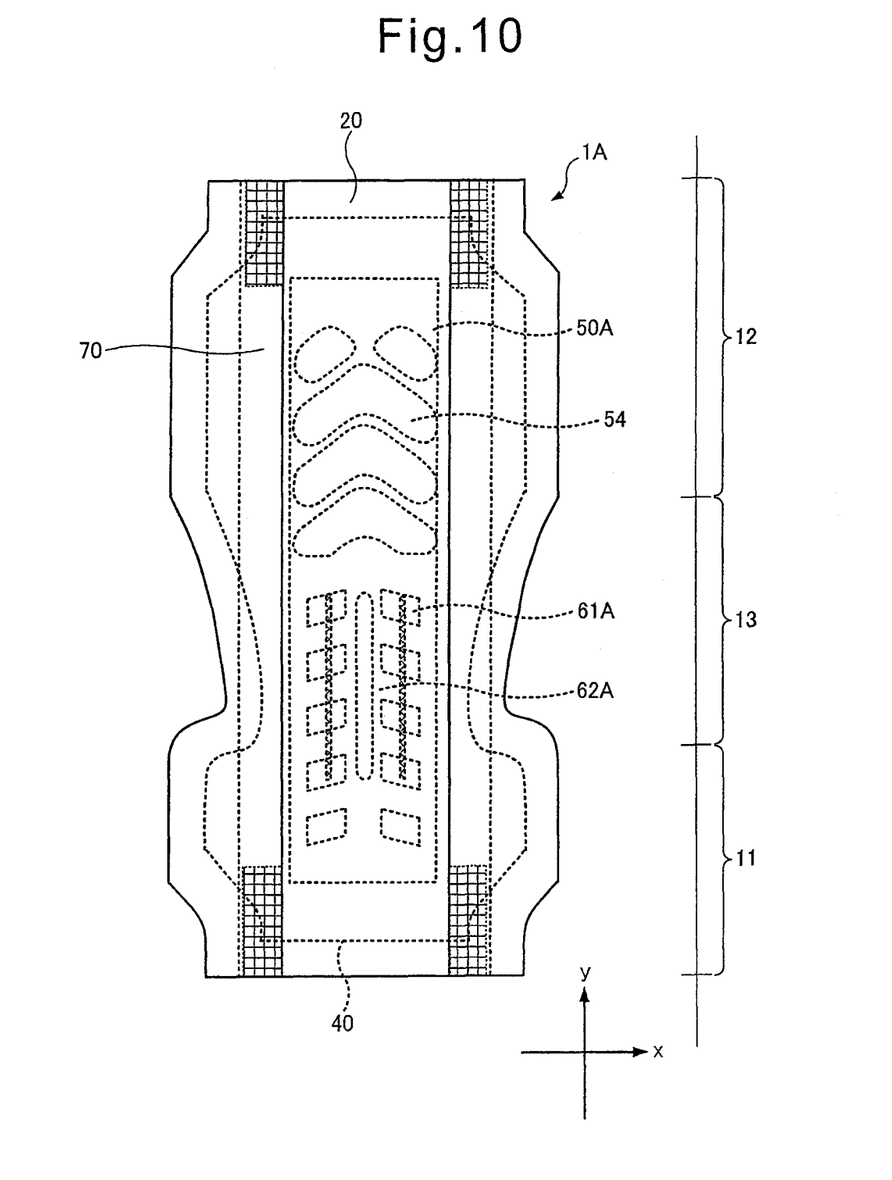
FIG. 10 is a view showing a modification example of the absorbent article according to one embodiment of the present invention.

(1) As in the absorbent article 1A shown in FIG. 10, the absorbent sheet 50A may be disposed across the front waist region 11, the crotch region 13 and the rear waist region 12. In this case, when the wearer's urination orifice is contacted with the absorbent article 1, for causing the excreted urine to be absorbed by the absorption body 40, an absorbent polymer-existing region 61A is preferably not disposed in the widthwise central region of the absorbent article 1A on the front waist region 11 side relative to the longitudinal center of the crotch region 13 of the absorbent sheet 50A. For example, as in the absorbent article 1A shown in FIG. 10, a configuration where in the widthwise central region of the absorbent article 1A on the front waist region 11 side relative to the longitudinal center of the crotch region 13 of the absorbent sheet 50A, a plurality of absorbent polymer-existing regions 61A aligned in the longitudinal direction are disposed on both sides and an absorbent polymer-nonexisting region 62A is disposed in the widthwise center of the absorbent article 1A may be employed. Thanks to this configuration, when the wearer's urination orifice is contacted with the absorbent article 1 and the absorption of urine by the absorption body 40 cannot keep up with the excretion of urine, the absorption of urine by the absorbent sheet 50A can prevent the urine from leaking out of the front waist region 11 and the crotch region 13 of the absorbent article 1A. In a next embodiment, it is possible to take a configuration where an absorbent sheet 50A is not provided in the widthwise central region of the absorbent article 1A. As a further alternative embodiment, the absorbent sheet 50A may be designed to allow its laying across the front waist region 11, the crotch region 13 and the rear waist region 12 by adding a separate absorbent sheet on the front waist region 11 side relative to the longitudinal center of the crotch region 13 of the absorbent sheet 50A.

Figure 11:
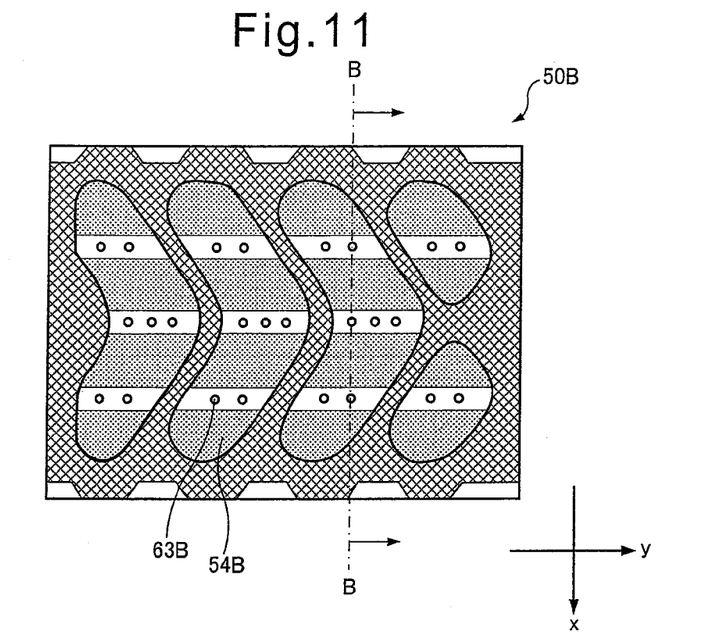
FIG. 11 is a view showing a modification example of the absorbent sheet in the absorbent article according to one embodiment of the present invention.
Figure 12A:
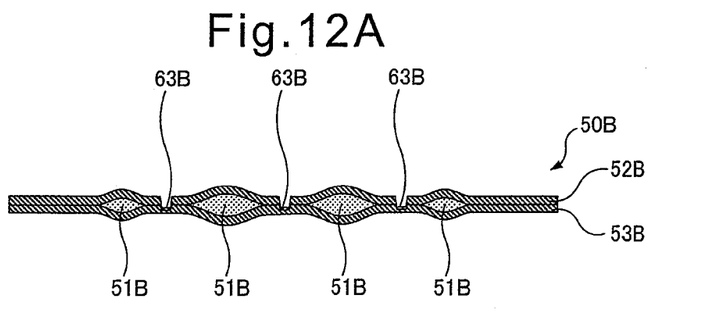
FIG. 12A is a view for explaining temporary attachment in the modification example of the absorbent sheet in the absorbent article according to one embodiment of the present invention.
Figure 12B:
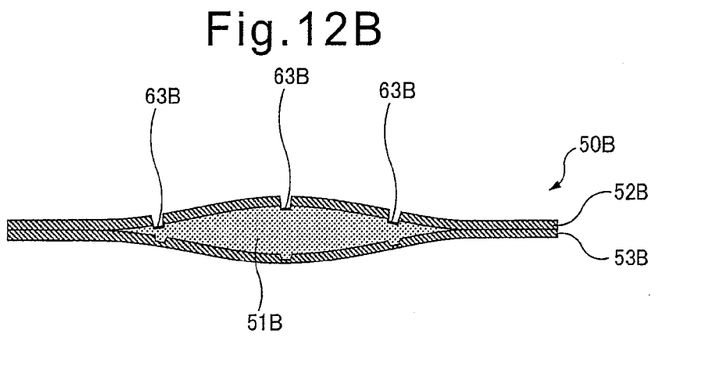
FIG. 12B is a view for explaining temporary attachment in the modification example of the absorbent sheet in the absorbent article according to one embodiment of the present invention.

(2) As in the absorbent sheet 50B of the embodiment shown in FIG. 11, temporary tacking 63B is performed to divide the absorbent polymer-existing region into a plurality of segmented regions (hereinafter referred to as a segment region), for example, into four segment regions. Thanks to this configuration, the absorbent polymer in the absorbent polymer-existing region 54B can be prevented from being present disproportionately in a part of the absorbent polymer-existing region 54B. The temporary tacking 63B indicates joining 63B where as shown in FIG. 12A, the upper liquid-pervious sheet 52B is joined with the lower liquid-pervious sheet 53B before the absorbent polymer 51B swell, but as shown in FIG. 12B, the joining is released when the absorbent polymer 51B swells. For the temporary tacking 63B, joint means such as heat seal, sonic seal and adhesive may be used. In the widthwise center of the absorbent polymer-existing region 54B of the absorbent sheet 50B shown in FIG. 11, temporary tacking 63B is provided by three heat seals, and on both widthwise sides relative to the widthwise center, temporary tacking 63B is provided by two heat seals. Incidentally, division of the absorbent polymer-existing region 54B by temporary tacking is not limited to division into four segment regions. It may be divided into two or more segment regions. Also, as long as the upper liquid-pervious sheet 52B is joined with the lower liquid-pervious sheet 53B by the temporary tacking 63B, an absorbent polymer may be present around the temporary tacking 63B. The temporary tacking 63B in the absorbent sheet 50B can be formed by diminishing the bonding strength between the liquid-pervious sheets enough to allow the liquid-pervious sheets to be separated from each other due to swelling of the absorbent polymer. Temporary tacking may be formed in a folded liquid-pervious sheet having sandwiched thereby the absorbent polymer. That is to say, temporary tacking may be formed in at least one liquid-pervious sheet having sandwiched thereby the absorbent polymer.

Figure 13:
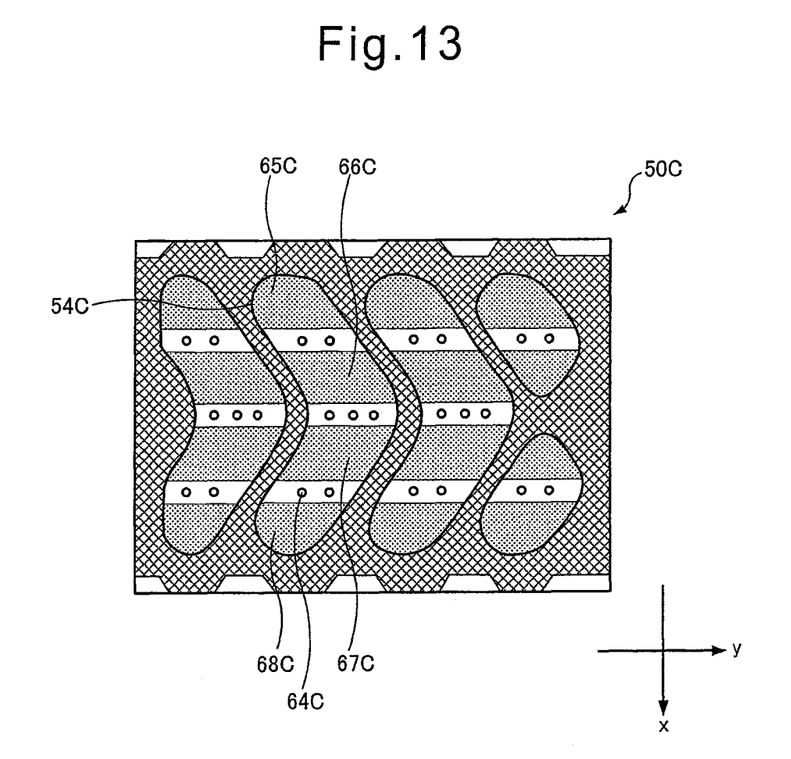
FIG. 13 is a view showing a modification example of the absorbent sheet in the absorbent article according to one embodiment of the present invention.

(3) As in the absorbent sheet 50C shown in FIG. 13, joining 64C may be performed to divide the absorbent polymer-existing region 54C into a plurality of segmented regions (hereinafter, referred to as a segment region), for example, into four segment regions 65C to 68C. Joining 64C may be the above-described temporary tacking or may be joining that is not released even when the absorbent polymer in the absorbent polymer-existing region 54C is swelled. Also, the amount of the absorbent polymer charged into each segment region of the absorbent polymer-existing region 54C divided into a plurality of segment regions in the width direction may be larger in the segment region located closer to the widthwise center of the absorbent sheet 50C and smaller as it proceeds widthwise outward relative to the widthwise center. That is, the amount of the absorbent polymer charged into the segment region 66C of the absorbent polymer-existing region 54C may be larger than the amount of the absorbent polymer charged into the segment region 65C of the absorbent polymer-existing region 54C, and the amount of the absorbent polymer charged into the segment region 67C of the absorbent polymer-existing region 54C may be larger than the amount of the absorbent polymer charged into the segment region 68C of the absorbent polymer-existing region 54C. In this case, the thickness of the absorbent sheet 50C is largest in the widthwise central region of the absorbent sheet 50C and decreases as it proceeds widthwise outward and therefore, the absorbent article having provided therein the absorbent sheet 50C comes to more fit the wearer's buttocks. In the absorbent sheet 50C shown in FIG. 13, joining 64C by three heat seals is provided in the widthwise center of the absorbent polymer-existing region 54C, and joining 64C by two heat seals is provided on both widthwise sides relative to the widthwise center. Incidentally, division of the absorbent polymer-existing region by the above-described joining is not limited to division into four segment regions. It may be divided into two or more segment regions. Also, as long as the upper liquid-pervious sheet is joined with the lower liquid-pervious sheet by the joining 64C, an absorbent polymer may be present around the joining 64C. The widthwise lengths of the regions 65C to 68C aligning in the width direction of the absorbent polymer-existing region 54C may be the same or different.

(4) In the above-described absorbent article 1 according to one embodiment, at the widthwise central position of the absorption body 40, a penetration part 41 longitudinally extending across from the front waist region 11 to the crotch region 13 is provided in the absorption body 40, but in place of the penetration part 41, a groove part where the absorption body 40 is dented from the topsheet 20 side surface of the absorption body 40 and thereby reduced in the thickness may be provided.

(5) In the above-described absorbent article 1 according to one embodiment, one absorption body 40 is disposed in the absorbent article 1, but two or more absorption bodies may be disposed in the absorbent article. For example, in place of the absorption body 40, a stack prepared by stacking two absorption bodies in the thickness direction may be disposed in the absorbent article. Also, in this case, out of two absorption bodies, the penetration part or groove part may be provided only in the absorption body on the topsheet side.

(6) The penetration part 41 or groove part of the absorption body 40 may be designed to longitudinally extend even into the region of the absorption body, where the absorbent sheet 50 is disposed. Thanks to this configuration, the excreted urine can rapidly move to the lower side of the absorbent sheet 50 and therefore, a larger amount of urine absorbed by the absorption body 40 is less likely to reach the wearer's skin side due to the absorbent sheet 50.

The present invention is not limited to the urine-absorbing pad. The present invention may be, for example, an absorbent article such as disposable diaper, toilet training pant and incontinence brief.

It is also possible to combine the embodiment with one modification example or a plurality of modification examples. Modification examples may be also combined with each other in any combination.

The descriptions in the foregoing pages are only one example, and the invention is not limited to the above-described embodiments by any means.

DESCRIPTION OF NUMERICAL REFERENCES

1, 1A Absorbent article
20 Topsheet
30 Backsheet
31 Hot-melt adhesive
40 Absorption body
41 Penetration part
42 Compressed groove
50, 50A to 50C Absorbent sheet
51, 51B, 320 Absorbent polymer
52, 52B, 322 Upper liquid-pervious sheet
53, 53B, 312 Lower liquid-pervious sheet
54, 54B, 61A Absorbent polymer-existing region
55, 62A Absorbent polymer-nonexisting region
56 Adhesive part
63B Temporary tacking
64C Joining
65C to 68C Segment region
70 Leak-preventive cuff
71 Edge part
72 Elastic body
314 Suction drum
316 Duct
318 Polymer charge tube
324 Heat sealing device

The invention claimed is:

1. An absorbent article consisting of a front waist region, a rear waist region and a crotch region located between the front and rear regions in a longitudinal direction from a front side to a rear side, comprising:
   a liquid-pervious topsheet,
   a backsheet,
   an absorption body intervening between said topsheet and said backsheet, and
   an absorbent sheet between said topsheet and said absorption body, comprising at least one liquid-pervious sheet having sandwiched thereby an absorbent polymer,
wherein:
   said absorbent sheet has at least one absorbent polymer-existing region in which said absorbent polymer is sandwiched by said at least one liquid-pervious sheet and at least one absorbent polymer-nonexisting region which is free of absorbent polymer,
   at least a part of said absorbent sheet is disposed in said rear waist region, and
   a planar shape of said absorbent polymer-existing region disposed on said rear waist region side of the longitudinal center in said crotch region of said absorbent sheet is a nearly V-shaped with an apex facing in the direction from said front waist region to said rear waist region in the longitudinal direction of said absorbent article.

2. The absorbent article as claimed in claim 1, wherein said at least one liquid-pervious sheet is a folded liquid-pervious sheet or two liquid-pervious sheets.

3. The absorbent article as claimed in claim 2, wherein:
   said absorbent polymer-existing region is divided into a plurality of segment regions by temporary tacking means joining said at least one liquid-pervious sheet sandwiching said absorbent polymer thereby.

4. The absorbent article as claimed in claim 3, wherein:
   said absorbent polymer-existing region is divided into a plurality of segment regions aligning in the width direction of said absorbent article, by joint means joining two liquid-pervious sheets sandwiching said absorbent polymer therebetween of said absorbent sheet, and
   the amount of the absorbent polymer charged into said plurality of segment regions is larger as the segment region is located closer to a widthwise center of said absorbent article and smaller as located further widthwise outward relative to the widthwise center.

5. The absorbent article as claimed in claim 4, wherein:
   a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

6. The absorbent article as claimed in claim 3, wherein:
   a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

7. The absorbent article as claimed in claim 2, wherein:
   said absorbent polymer-existing region is divided into a plurality of segment regions aligning in the width direction of said absorbent article, by joint means joining two liquid-pervious sheets sandwiching said absorbent polymer therebetween of said absorbent sheet, and
   the amount of the absorbent polymer charged into said plurality of segment regions is larger as the segment region is located closer to a widthwise center of said absorbent article and smaller as located further widthwise outward relative to the widthwise center.

8. The absorbent article as claimed in claim 7, wherein:
   a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

9. The absorbent article as claimed in claim 2, wherein:
a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

10. The absorbent article as claimed in claim 9, wherein:
a plurality of adhesive parts extending in the longitudinal direction of said absorbent article and aligning in the width direction of said absorbent article are provided on each of said liquid-pervious sheet surfaces sandwiching said absorbent polymer therebetween at least in the absorbent polymer-existing region of said absorbent sheet, and
an adhesive part-to-adhesive part distance between adjacent adhesive parts out of the adhesive parts provided on the liquid-pervious sheet on the absorption body side in said absorbent sheet is smaller than an adhesive part-to-adhesive part distance of the adhesive parts provided on the liquid-pervious sheet on the topsheet side in said absorbent sheet.

11. The absorbent article as claimed in claim 1, wherein:
said absorbent polymer-existing region is divided into a plurality of segment regions by temporary tacking means joining said at least one liquid-pervious sheet sandwiching said absorbent polymer thereby.

12. The absorbent article as claimed in claim 11, wherein:
said absorbent polymer-existing region is divided into a plurality of segment regions aligning in the width direction of said absorbent article, by joint means joining two liquid-pervious sheets sandwiching said absorbent polymer therebetween of said absorbent sheet, and
the amount of the absorbent polymer charged into said plurality of segment regions is larger as the segment region is located closer to a widthwise center of said absorbent article and smaller as located further widthwise outward relative to the widthwise center.

13. The absorbent article as claimed in claim 12, wherein:
a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

14. The absorbent article as claimed in claim 11, wherein:
a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

15. The absorbent article as claimed in claim 1, wherein:
said absorbent polymer-existing region is divided into a plurality of segment regions aligning in the width direction of said absorbent article, by joint means joining two liquid-pervious sheets sandwiching said absorbent polymer therebetween of said absorbent sheet, and
the amount of the absorbent polymer charged into said plurality of segment regions is larger as the segment region is located closer to a widthwise center of said absorbent article and smaller as located further widthwise outward relative to the widthwise center.

16. The absorbent article as claimed in claim 15, wherein:
a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

17. The absorbent article as claimed in claim 1, wherein:
a plurality of adhesive parts extending in the longitudinal direction of said absorbent article and aligning in a width direction of said absorbent article are provided on at least one of the liquid-pervious sheet surfaces sandwiching said absorbent polymer therebetween at least in the absorbent polymer-existing region of said absorbent sheet.

18. The absorbent article as claimed in claim 17, wherein:
a plurality of adhesive parts extending in the longitudinal direction of said absorbent article and aligning in the width direction of said absorbent article are provided on each of said liquid-pervious sheet surfaces sandwiching said absorbent polymer therebetween at least in the absorbent polymer-existing region of said absorbent sheet, and
an adhesive part-to-adhesive part distance between adjacent adhesive parts out of the adhesive parts provided on the liquid-pervious sheet on the absorption body side in said absorbent sheet is smaller than an adhesive part-to-adhesive part distance of the adhesive parts provided on the liquid-pervious sheet on the topsheet side in said absorbent sheet.

19. The absorbent article as claimed in claim 1, wherein said absorbent polymer-existing region is tilted at an angle between 45° and 80° relative to the straight line extending in the longitudinal direction of said absorbent article.

20. The absorbent article as claimed in claim 1, wherein said absorbent sheet is disposed across the front waist region, the crotch region and the rear waist region.

* * * * *